(12) United States Patent
Mitra et al.

(10) Patent No.: US 8,551,531 B2
(45) Date of Patent: Oct. 8, 2013

(54) PENTABLOCK POLYMERS

(75) Inventors: Ashim K. Mitra, Overland Park, KS (US); Gyan Prakash Mishra, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 441 days.

(21) Appl. No.: 12/758,541

(22) Filed: Apr. 12, 2010

(65) Prior Publication Data

US 2011/0250283 A1 Oct. 13, 2011

(51) Int. Cl.
- A61K 9/16 (2006.01)
- A61K 9/50 (2006.01)

(52) U.S. Cl.
- CPC .................................. A61K 9/5026 (2013.01)
- USPC ........................................................ 424/497

(58) Field of Classification Search
None
See application file for complete search history.

(56) References Cited

U.S. PATENT DOCUMENTS

| | | | | |
|---|---|---|---|---|
| 5,442,016 | A * | 8/1995 | Jarrett et al. | 525/415 |
| 5,702,717 | A | 12/1997 | Cha et al. | |
| 6,056,970 | A | 5/2000 | Greenawalt et al. | |
| 6,201,072 | B1 | 3/2001 | Rathi et al. | |
| 6,410,645 | B1 | 6/2002 | Pathak et al. | |
| 6,800,663 | B2 * | 10/2004 | Asgarzadeh et al. | 516/108 |
| 2004/0185104 | A1 | 9/2004 | Piao et al. | |
| 2005/0238722 | A1 | 10/2005 | Pathak et al. | |
| 2006/0034889 | A1 | 2/2006 | Jo et al. | |
| 2008/0293827 | A1 * | 11/2008 | Lee et al. | 514/772.3 |
| 2011/0071216 | A1 | 3/2011 | Fowers et al. | |

FOREIGN PATENT DOCUMENTS

WO WO 2009/126442 * 10/2009

OTHER PUBLICATIONS

Deng, et al., Synthesis and Characterization of Biodegradable Block Copolymers of 1-Caprolactone and D,L-Lactide Initiated by Potassium Poly(ethylene glycol )ate, J. Polymer Sci Part A: Polymer Chemistry 35(4) 703-708 (1997).

Kim et al., The Synthesis and Biodegradable behavior of PLA-PCL-PEG-PCL-PLA Multi Block Copolymer, Polymer Preprints, Japan 49(7) 1557-1558 (2000) [abstract only].

Huang, *Polymeres bioresorbables derives de la Poly($\epsilon$-caprolactone) en ingenierrie tissulaire*, Thesis (Dec. 2004).

Huang, *Polymeres bioresorbables derives de la Poly($\epsilon$-caprolactone) en ingenierrie tissulaire*, PowerPoint (Dec. 2004) [downloaded from web site www.huangminghsi.com/minghsi/these_orale.pdf on Apr. 21, 2008—no longer available].

Hwang et al., *Caprolactonic Poloxamer Analog: PEG-PCL-PEG*, Biomacromolecules 6 885-890 (2005).

Huang, et al., *Degradation Characteristics of Poly($\epsilon$-caprolactone)-Based Copolymers and Blends*, J. Applied Polymer 102(2) 1681-1687 (2006).

Liu et al., *Thermoreversible gel-sol behavior of biodegradable PCL-PEG-PCL triblock copolymer in aqueous solutions*, Journal of Biomedical Materials Research Part B: Applied Biomaterials 165-175 (2007).

Gong et al., Thermosensitive PEG-PCL-PEG Hydrogel Controlled Drug Delivery System: Sol-Gel-Sol Transition and In Vitro Drug Release Study, J. Pharma. Sciences 98:(10) 3707-3717 (2009).

(Continued)

Primary Examiner — Brian Gulledge
(74) Attorney, Agent, or Firm — Stinson Morrison Hecker LLP

(57) ABSTRACT

Novel pentablock polymers comprising PGA-PCL-PEG-PCL-PGA or PEG-PCL-PLA-PCL-PEG, wherein PEG is polyethylene glycol, PCL is poly($\epsilon$-caprolactone), PGA is poly(glycolic acid), and PLA is poly(lactic acid).

20 Claims, 5 Drawing Sheets

(56) References Cited

OTHER PUBLICATIONS

Gong et al., *Synthesis and characterization of PEG-PCL-PEG thermosensitive hydrogel*, Int'l Journal of Pharmaceutics 365 89-99 (2009).

Sawhney et al., *Rapidly degraded terpolymers of DL-lactide, glycolide, and E-caprolactone with increased hydrophilicity by copolymerization with polyethers*, J. Biomed. Mater. Res. 24 1397-1411, 1990.

International Search Report/Written Opinion for PCT/US11/55970 dated Mar. 2, 2012.

* cited by examiner

PENTABLOCK POLYMERS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to novel pentablock polymers. The pentablock polymers are biocompatible and biodegradable, and thus the pentablock polymers may be used for the administration of biologically active agents or diagnostic agents, especially hydrophilic compounds such as peptides and proteins. More particularly, this invention relates to biocompatible and biodegradable polymers useful for administering peptide or protein drugs to a subject and to a process for preparing the same. The present invention is also directed to nanoparticles and thermosensitive gels of such pentablock polymers.

2. Description of Related Art

Various block polymers are known in the art. For example, Cha et al., U.S. Pat. No. 5,702,717 discloses several triblock polymers, such as the PCL-PEG-PCL and PLA-PEG-PLA triblock polymer comprised of polyethylene glycol ("PEG") and poly(ε-caprolactone) ("PCL"), and polylactide ("PLA"). See also Lui et al., *Thermoreversible gel-sol behavior of biodegradable PCL-PEG-PCL triblock copolymer in aqueous solutions*, J. Biomed. Mater. Res. B. Appl. Biomater. January 84 (1) 165-75 (2008). These polymers forming the block polymer are all well-known FDA-approved biodegradable and biocompatible materials. In addition, the pentablock polymer PLA-PCL-PEG-PCL-PLA has been studied. See Deng et al., *Synthesis and Characterization of Block Polymers of ε-Caprolactone and DL-Lactide Initiated by Ethylene Glycol or Poly(ethylene glycol)*, J. Polymer Sci. Vol 35 No. 4 703-708 (1997); Kim et al., *The Synthesis and Biodegradable behavior of PLA-PCL-PEG-PCL-PLA Multi Block Copolymer*, Polymer Preprints, Vol. 49 No. 7 1557-1558 (2000). These insoluble polymers were proposed as tissue scaffolds by Huang in a PowerPoint presentation accessed on the Internet in April 2008, *Polymeres Bioresorbables Dérivés de Poly (ε-caprolactone) en Ingénierie Tissulaire*, Centre de Recherche surles Biopolyméres Artificiels, UMR CNRS 5473 Faculté de Pharmacie, Université Montpellier I en collaboration avec Division de Bioingénierie, Université Nationale de Singapour.

BRIEF SUMMARY OF THE INVENTION

The present invention is directed to novel pentablock polymers useful for the delivery of bioactive agents and/or diagnostic agents (especially proteins and peptides) useful in the treatment or diagnosis of a wide number of disorders or diseases.

In one aspect, the present invention is directed to novel pentablock polymers which are useful for forming nanoparticles with the bioactive agent and/or diagnostic agent encapsulated therein. Typically, the nanoparticles are ideal for drug delivery in which the drug release exhibits first order kinetics. The pentablock polymers are defined according to the formula:

$$PGA_z\text{-}PCL_y\text{-}PEG_x\text{-}PCL_y\text{-}PGA_z,$$

wherein PEG is polyethylene glycol;
wherein PCL is poly(ε-caprolactone);
wherein PGA is polyglycolic acid;
wherein X defines an average molecular weight of 200 to 20,000 Da;
wherein Y defines an average molecular weight of 1,000 to 20,000 Da; and
wherein Z defines an average molecular weight of 100 to 5,000 Da.

In another aspect, the present invention is directed to novel pentablock polymers which are useful for forming thermosensitive gels having the bioactive agent and/or diagnostic agent contained with the gel. Typically, the thermosensitive gel is ideal for drug delivery in which the drug release exhibits zero order kinetics. The pentablock polymers are defined according to the formula:

$$PEG_w\text{-}PCL_v\text{-}PLA_{1/2u}\text{-}LINKER\text{-}PLA_{1/2u}\text{-}PCL_v\text{-}PEG_w,$$

wherein PLA is polylactic acid;
wherein PCL is poly(ε-caprolactone);
wherein PEG is polyethylene glycol;
wherein U defines an average molecular weight of 100 to 5,000 Da;
wherein V defines an average molecular weight of 100 to 1,000 Da;
wherein W defines an average molecular weight of 100 to 20,000 Da; and
wherein LINKER defines a linker.

The thermosensitive gel preferably has a lower crucial solution temperature below body temperature, and most preferably below about 35° C. Thus, in another aspect, the present invention is directed to an injectable drug delivery liquid composition having reverse thermal gelation properties comprising the thermosensitive pentablock polymers, a pharmaceutically acceptable liquid carrier, and an effective amount of a bioactive agent or diagnostic agent. In one aspect, the pentablock polymer comprises about 1 to 50 wt % of the composition. In still another aspect, the pharmaceutically acceptable liquids carrier is selected from the group consisting of PBS, saline, and dextrose solutions.

In still another aspect, the nanoparticles and thermosensitive gel may be combined to form yet another controlled release formulation. In one aspect, the drug or diagnostic agent is encapsulated in the nanoparticles. In turn, these nanoparticles are dispersed in the thermosensitive gel. Thus, in one aspect, the present invention is directed to a controlled release formulation comprising a plurality of nanoparticles. The nanoparticles comprise a drug or diagnostic agent encapsulated in a pentablock polymer according to $PGA_z\text{-}PCL_y\text{-}PEG_x\text{-}PCL_y\text{-}PGA_z$, wherein PEG is polyethylene glycol; wherein PCL is poly(ε-caprolactone); wherein PGA is polyglycolic acid; wherein X defines an average molecular weight of 200 to 20,000 Da; wherein Y defines an average molecular weight of 1,000 to 20,000 Da; and wherein Z defines an average molecular weight of 100 to 5,000 Da. These nanoparticles are then dispersed in a thermosensitive gel comprising second pentablock polymer according to $PEG_w\text{-}PCL_v\text{-}PLA_{1/2u}\text{-}LINKER\text{-}PLA_{1/2u}\text{-}PCL_v\text{-}PEG_w$, wherein PLA is polylactic acid; wherein PCL is poly(ε-caprolactone); wherein PEG is polyethylene glycol; wherein U defines an average molecular weight of 100 to 5,000 Da; wherein V defines an average molecular weight of 100 to 1,000 Da;

wherein W defines an average molecular weight of 100 to 20,000 Da; and wherein LINKER defines a linker.

In still a further aspect, the present invention is directed to various methods of delivering bioactive agents or diagnostic agents using the pentablock polymers of the present invention (the nanoparticles, the thermosensitive gels, and combinations thereof). Thus, in one aspect, the present invention is directed to a method for the parenteral delivery of a bioactive agent or diagnostic agent to a subject comprising: (a) providing a pharmaceutical composition comprising an effective amount of the bioactive agent or diagnostic agent and the pentablock polymer $PEG_w$-$PCL_v$-$PLA_{1/2u}$-LINKER-$PLA_{1/2u}$-$PCL_v$-$PEG_w$ as defined herein and (b) administering the pharmaceutical composition to the patient. The composition is preferably administered to the subject intramuscularly or subcutaneously. In a preferred aspect, the method includes the steps of providing an injectable drug delivery liquid having reverse thermal gelation properties, such that the liquid comprises an aqueous solution comprising an effective amount of a bioactive agent or diagnostic agent contained in the pentablock polymer $PEG_w$-$PCL_v$-$PLA_{1/2u}$-LINKER-$PLA_{1/2u}$-$PCL_v$-$PEG_w$, wherein the pentablock polymer has a LCST below the body temperature of the subject. The method also includes the step of maintaining the drug delivery liquid at a temperature below the LCST of the pentablock polymer. Next, the method includes the step of injecting said drug delivery liquid parenterally into the subject to form a gel depot of said drug and pentablock polymer as the temperature of the liquid is raised by the body temperature of said subject to be above the LCST of said polymer.

In yet another aspect, the present invention is directed to a method for delivering a bioactive agent or diagnostic agent using a combination of nanoparticles dispersed in the thermosensitive gels of the present invention.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
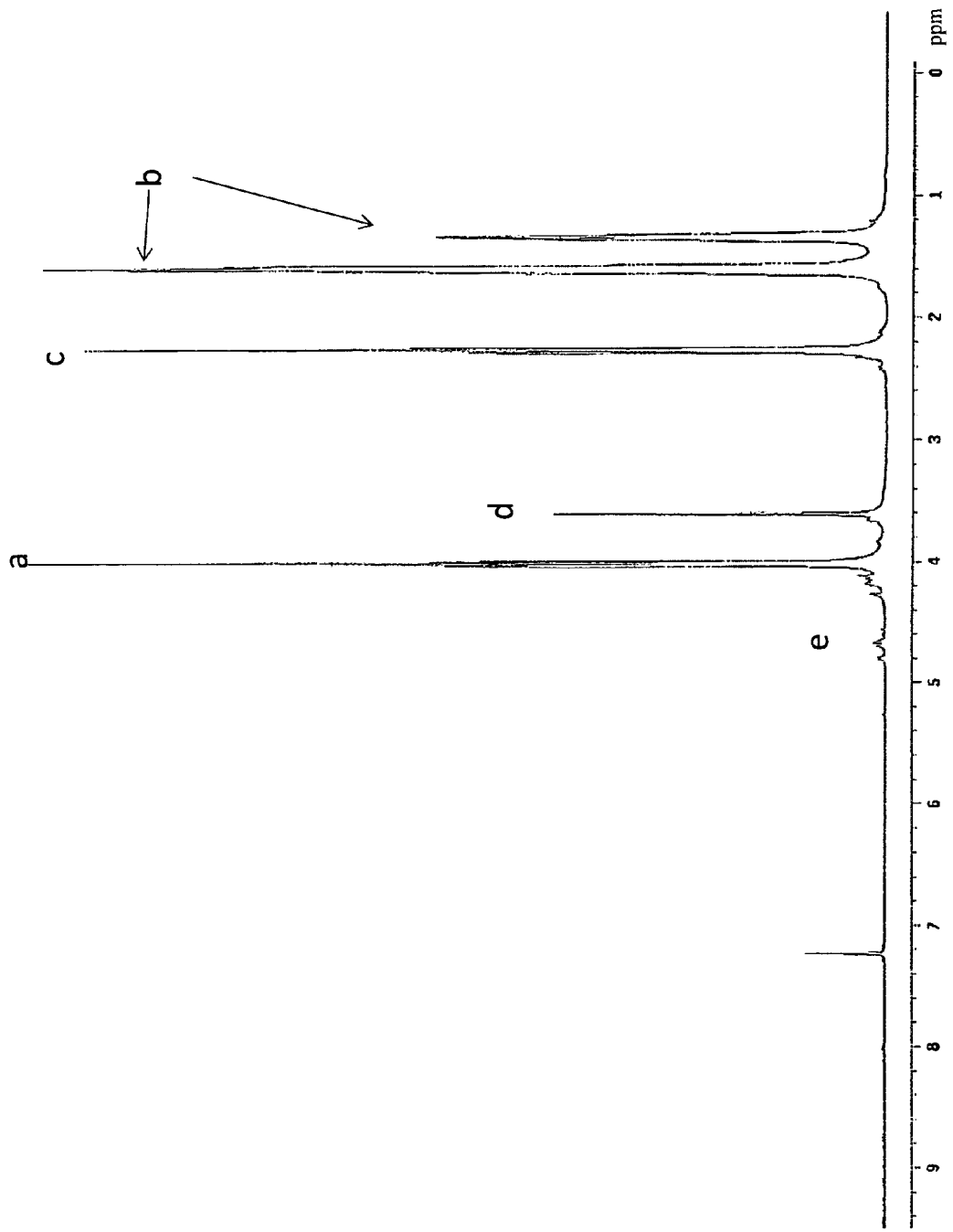
FIG. 1 shows the NMR spectra of Pentablock Polymer A ($PGA_{300}$-$PCL_{7500}$-$PEG_{1000}$-$PCL_{7500}$-$PGA_{300}$).

The present invention is directed to novel pentablock polymers useful for drug delivery systems. The polymers are biodegradable and biocompatible. Many of the pentablock polymers may be used to form nanoparticles with a bioactive agent or diagnostic agent contained therein. Many of the pentablock polymers exhibit reverse thermal gelation behavior, and possess good drug release characteristics.

The present invention is also directed to methods for fabricating the pentablock polymers of the present invention, as well as compositions comprising the biodegradable and biocompatible pentablock polymers with a hydrophilic drug, such as a peptide. The present invention is well adapted for the administration of the hydrophilic drugs and particularly highly water-soluble peptide and protein drugs. The drugs are released at a controlled rate with the corresponding biodegradation of the polymeric matrix.

As used herein, "administering" and similar terms mean delivering the composition to an individual being treated. Preferably, the compositions comprising the pentablock polymers of the present invention are administered by the subcutaneous, intramuscular, transdermal, oral, transmucosal, or intraperitoneal routes.

"Biocompatible" means materials or the intermediates or end products of materials formed by solubilization hydrolysis, or by the action of biologically formed entities which can be enzymes or other products of the organism and which cause no adverse effect on the body.

"Biodegradable" means that the pentablock polymer can break down or degrade within the body to non-toxic components after all bioactive agent or diagnostic agent has been released.

"Depot" means a drug delivery liquid following injection into a warm-blooded animal which has formed a gel upon the temperature being raised to or above the LCST.

"Drug" or "bioactive agent" shall mean any organic compound or substance having bioactivity and adapted or used for a therapeutic purpose.

"Drug delivery liquid" or "drug delivery liquid having reverse thermal gelation properties" shall mean a "solution" suitable for injection into a warm-blooded animal which forms a depot upon having the temperature raised above the LCST of the polymer.

An "effective amount" means the amount of bioactive agent or diagnostic agent that is sufficient to provide the desired local or systemic effect at a reasonable risk/benefit ratio as would attend any medical treatment or diagnostic test. This will vary depending on the patient, the disease, the treatment being effected, and the nature of the agent.

"Gel," when used in reference to the pentablock polymers and/or drug combination at a temperature at or above the LCST, shall be inclusive of such combinations are generally semi-solid in nature.

"Hydrophilic" means the ability to dissolve in water. When used in the context of the hydrophilic drugs or diagnostic agents in the present invention, the term embraces a drug that is preferably sparingly soluble, more preferably soluble, still more preferably freely soluble, and still most preferably very soluble, according to USP-NF definitions.

"LCST" or "lower critical solution temperature," means the temperature at which the pentablock polymer undergoes reverse thermal gelation, i.e., the temperature below which the polymer is soluble in water and above which the pentablock polymer undergoes phase separation to form a semi-solid containing the drug and the pentablock polymer. The terms "LCST," "gelation temperature," and "reverse thermal gelation temperature," or the like shall be used interchangeably in referring to the LCST.

The term "nanoparticle" means a particle, the largest dimension of which is less than one micron, e.g., less than about 1,000 nm, 900 nm, 800 nm, 700 nm, 600 nm, 500 nm, 400 nm, 300 nm, 200 nm, 100 nm, 50 nm, etc. Thus, for example, the nanoparticles of the present invention may range between about 100 to 1,000 nm, 200 to 900 nm, 300 to 700 nm, and 400 to 600 nm.

"Parenteral" shall mean any route of administration other than the alimentary canal and shall specifically include intramuscular, intraperitoneal, intra-abdominal, subcutaneous, and, to the extent feasible, intravenous.

"Pharmaceutically acceptable" means that which is useful in preparing a pharmaceutical composition that is generally safe, non-toxic, and neither biologically nor otherwise undesirable and includes that which is acceptable for veterinary use as well as human pharmaceutical use. Examples of "pharmaceutically acceptable liquid carriers" include water an organic solvents. Preferred pharmaceutically acceptable aqueous liquids include PBS, saline, and dextrose solutions.

"Peptide", "polypeptide", "oligopeptide," and "protein" shall be used interchangeably when referring to peptide or protein drugs and shall not be limited as to any particular molecular weight, peptide sequence or length, field of bioactivity, diagnostic use, or therapeutic use unless specifically stated.

"Solution," "aqueous solution," and the like, when used in reference to a combination of drug and pentablock polymer contained in such solution, shall mean a water-based solution having such drug/polymer combination dissolved or uniformly suspended therein at a functional concentration and maintained at a temperature below the LCST of the block polymer.

The term "thermosensitive" refers to a polymer which exists as a generally clear solution near ambient temperature in water but when the temperature is raised the LCST (which is preferably about body temperature), interact to form a gel, emulsion, or suspension.

The term "treatment" or "treating" means administration of a drug for purposes including: (i) preventing the disease or condition, that is, causing the clinical symptoms of the disease or condition not to develop; (ii) inhibiting the disease or condition, that is, arresting the development of clinical symptoms; and/or (iii) relieving the disease or condition, that is, causing the regression of clinical symptoms.

Below, the exemplary embodiments are shown and specific language will be used herein to describe the same. It should nevertheless be understood that no limitation of the scope of the invention is thereby intended. Alterations and further modifications of the inventive features illustrated herein, and additional applications of the principles of the present invention as illustrated herein, for one skilled in the relevant art, in connection with this disclosure, should be considered within the scope of the present invention.

The present invention is directed to a novel pentablock polymer comprised of (1) PEG, (2) PCL, and (3) PGA or PLA. Generally, the block polymer will be a pentablock polymer, i.e., a CBABC type block polymer.

Nanoparticles

For preparation of the pentablock polymer used for nanoparticles of the present invention, the pentablock polymer preferably has a PGA-PCL-PEG-PCL-PGA configuration.

The hydrophilic A block segment is preferably PEG having an average molecular weight of between about 200 to 20,000 Da and more preferably has an average molecular weight between about 500 and 5,000 Da, and still more preferably has an average molecular weight between about 500 to 1,500 Da, and most preferably has an average molecular weight of about 1,000 Da.

The hydrophobic B block segment is preferably derived from a cyclic lactone, and is most preferably derived from ε-caprolactone. Thus, the B block segment comprises PCL having an average molecular weight of between about 1,000 Da to 20,000 Da, more preferably between about 2,500 to 15,000 Da, still more preferably about 5,000 to 10,000 Da, and most preferably about 7,500 Da. In another aspect, the average molecular weight of the hydrophobic B block segment is preferably greater than about 1,000 Da (for example, the B block segment may have an average molecular weight of about 2,000 Da, 3,000 Da, 4,000 Da, 5,000 Da, 6,000 Da, 7,000 Da, 8,000 Da, 9,000 Da, 10,000 Da, 12,000 Da, 15,000 Da, 20,000 Da or some range therebetween).

The hydrophobic C block segment is preferably derived from a glycolide. The C block segment preferably comprises PGA having an average molecular weight of between about 100 to 5,000 Da, still more preferably between about 200 to 1,000 Da, still more preferably between about 200 and 800 Da (for example, the C block segment may have an average molecular weight of about 200 Da, 300 Da, 400 Da, 500 Da, 600 Da, 700 Da, 800 Da or some range therebetween). Molecular weights in the range of about 200 to 500 Da are most preferred. While the PGA segment is considered hydrophobic, it is sufficiently hydrophilic to interact with hydrophilic drugs.

Thus, in one aspect, a pentablock polymers used to make nanoparticles in accordance with the present invention may be defined according to the following formula:

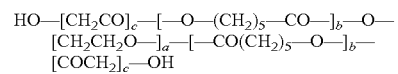

wherein a, b, and c are integers such that the polymer can be defined according to:

wherein X defines an average molecular weight of 200 to 20,000 Da, preferably 500 to 5,000 Da, still more preferably 500 to 1,500 Da, and most preferably 1,000 Da;

wherein Y defines an average molecular weight of 1,000 Da to 20,000 Da, preferably 2,500 to 15,000 Da, still more preferably 5,000 to 10,000 Da, and most preferably 7,500 Da; and wherein Z defines an average molecular weight of 100 to 5,000 Da, preferably 200 to 1,000 Da, still more preferably 200 to 800 Da, and most preferably 200 to 500 Da.

By varying the molecular weights of the various A, B, and C blocks, the pentablock polymers synthesized as disclosed herein have various hydrophobic and hydrophilic blocks, which may alter how the nanoparticles degrade in vitro and in vivo. In general, if the hydrophobic B block is greater than about 1,000 Da, nanoparticles are formed.

The hydrophilic A block and the hydrophobic B and C blocks are synthesized and utilized because of their biodegradable and biocompatible properties. The in vitro and in vivo degradation of these hydrophobic polymer blocks is well understood and the degradation products are natural metabolites that are readily eliminated by the body. Generally, for the preparation of nanoparticles, the hydrophilic A block (PEG block) should be less than 10% by weight, the B block (PCL block) should be greater than 80% by weight, and the C block (PGA block) should be less than 10% by weight.

As shown in the following examples, the pentablock polymer compounds of the present invention are ideally suited to form nanoparticles, which may encapsulate an effective amount bioactive agent or diagnostic agent. Examples of such agents are disclosed below. The nanoparticles comprising the pentablock polymers of the present invention provide for controlled or extended release of the bioactive agent or diagnostic agent. In general, the pentablock polymer can be designed to have a selected rate of drug release, and typically drug release from the nanoparticles exhibits first order drug release kinetics. The amount of drug or diagnostic agent loaded in the nanoparticles will depend upon the nature of the agent. However, the drug and/or diagnostic agent typically comprises about 0.01 to 50 wt % of the composition, more preferably about 0.1 to 10% wt of the composition, with about 1 to 5 wt % being most preferred.

Thermosensitive Gel

For preparation of the pentablock polymer used for the thermosensitive gels of the present invention, the pentablock polymer preferably has a PEG-PCL-PLA-PCL-PEG configuration.

The hydrophobic A block segment is preferably derived from a lactide. The A block segment preferably comprises PLA having an average molecular weight of between about 100 to 5,000 Da, more preferably between about 200 and 1,000 Da, and still more preferably between about 200 and 800 Da (for example, an average molecular weight of about 200 Da, 300 Da, 400 Da, 500 Da, 600 Da, 700 Da, 800 Da or some range therebetween). An average molecular weight in the range of about 400 to 600 Da is most preferred. It will be appreciated that in the preferred embodiment, a linker separates the hydrophobic A block, but that the average molecular weight referenced for this block refers to the combined molecular weights of the PLA blocks on both sides of the linker.

The hydrophobic B block segment is preferably derived from a cyclic lactone, and is most preferably derived from ε-caprolactone. Thus, in one aspect, the B block segment comprises PCL having an average molecular weight less than about 1,000 Da. For example, the B block segment is preferably PCL having an average molecular weight of between about 100 to 1,000 Da (for example, and average molecular weight of about 200 Da, 300 Da, 400 Da, 500 Da, 600 Da, 700 Da, 800 Da or some range therebetween), and more preferably has an average molecular weight between about 200 and 900 Da, and still more preferably has an average molecular weight between about 600 to 850 Da, and most preferably has an average molecular weight of about 825 Da.

The hydrophilic C block segment is preferably PEG having an average molecular weight of between about 100 to 20,000 Da and more preferably has an average molecular weight between about 200 to 5,000 Da, and still more preferably has an average molecular weight between about 300 to 2,000 Da, and most preferably has an average molecular weight of 550 Da.

Thus, in one aspect, a pentablock polymers used to make the thermosensitive gel in accordance with the present invention may be defined according to the following formula:

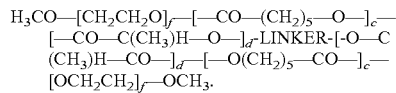

wherein d, e, and f are integers such that the polymer can be defined according to:

wherein U defines an average molecular weight of 100 to 5,000 Da, preferably 200 to 1,000 Da, still more preferably 200 to 800 Da, and most preferably 400 to 600 Da;

wherein V defines an average molecular weight of 100 to 1,000 Da, preferably 2,000 to 900 Da, and most preferably 600 to 850 Da;

wherein W defines an average molecular weight of 100 to 20,000 Da, preferably 200 to 5,000 Da, and most preferably 300 to 2,000 Da; and wherein LINKER defines a linker, which is preferably diisocyanate, for example 1,4-diisocyanatebutate, 1,4-diisocyante phenylene, or hexamethylene diisocyanate.

By varying the molecular weights of the various A, B, and C blocks, the pentablock polymers synthesized as disclosed herein have different hydrophobic and hydrophilic blocks, which may alter how the thermosensitive gel degrades in vitro and in vivo. In general, if the hydrophobic B block is less than about 1,000 Da, a thermosensitive gel is generally formed. The pentablock polymers possess targeted reverse thermal gelation properties and still be biodegradable and biocompatible.

The hydrophilic C block and the hydrophobic A and B blocks are synthesized and utilized because of their biodegradable and biocompatible properties. The in vitro and in vivo degradation of these hydrophobic polymer blocks is well understood and the degradation products are natural metabolites that are readily eliminated by the body. The molecular weight of the hydrophobic A and B blocks, relative to that of the water-soluble C block, is regulated to be sufficiently small to retain desirable water-solubility and gelling properties. In addition, for the preparation of gels, the proportionate weight ratios of hydrophilic C block to the more hydrophobic A and B blocks must also be sufficient to enable the block polymer to possess water solubility at temperatures below the LCST. Generally, for the preparation of gels, the C block (PEG block) should be about 10 to 50% by weight (preferably around 25 to 40 wt %), the 13 block (PCL block) should be about 40 to 60% by weight (preferably about 45 to 55 wt %), and the A block (PLA block) should be about 5 to 25% by weight (preferably about 10 to 20 wt %).

The mixture of the pentablock polymer used for thermosensitive gels and the bioactive agent or diagnostic agent may be prepared as an aqueous solution at a lower temperature than the gelation temperature of the pentablock polymer. In general, this may be performed by forming a solution of the pentablock polymer and the bioactive agent or diagnostic agent at a suitable temperature. The pentablock polymers are generally in solution at room temperature (typically about 20 to 26° C.) or at the desired storage temperature (e.g., refrigeration). Once parenterally injected into the body, e.g., via intramuscular, subcutaneous, or intraperitoneal route as a drug delivery liquid, the drug/polymer formulation will undergo a phase change and will preferably form a highly swollen gel since the body temperature (e.g., 37° C. for humans) will be above the gelation temperature of the material (typically about 30 to 35° C.). The LCST is thus preferably less than about 35, 34, 33, 32, 31, or 30° C. That is, the composition comprising the pentablock polymer forms a gel and solidifies into a depot as the temperature is raised due to the reverse gelation properties of the drug/polymer composition.

The pentablock polymer and bioactive agent or diagnostic agent system will cause minimal toxicity and mechanical irritation to the surrounding tissue due to the biocompatibility of the materials and will be completely biodegradable within a specific predetermined time interval. Once gelled, the release of the bioactive agent or diagnostic agent from the polymeric matrix can be controlled by proper formulation of the various polymer blocks.

The concentration at which the pentablock polymers are soluble at temperatures below the LCST may be considered as the functional concentration. Generally speaking, polymer concentrations of up to about 50% by weight can be used and still be functional. However, concentrations in the range of about 3 to 40% are preferred and concentrations in the range of about 10 to 25% by weight are most preferred. In order to obtain a viable phase transition of the polymer, a certain minimum concentration is required. At the lower functional concentration ranges the phase transition may result in the formation of an emulsion rather than a gel. At higher concentrations, a gel network is formed. The actual concentration at which an emulsion may phase into a gel network may vary according to the ratio of hydrophobic A and B blocks to hydrophilic C blocks and the composition and molecular weights of each of the blocks. Since both emulsions and gels can both be functional it is not imperative that the actual physical state be precisely determined. However, the formation of a swollen gel network is preferred.

The thermosensitive gels comprising the pentablock polymers of the present invention provide for controlled or extended release of the bioactive agent or diagnostic agent. In general, the pentablock polymer can be designed to have a selected rate of drug release, and typically drug release from the nanoparticles exhibits zero order drug release kinetics.

While the pentablock polymers of the present invention used to form thermosensitive gels are generally used in depot drug delivery, the pentablock polymers can also be used in a variety of therapeutic applications or diagnostic applications, including surgical applications. In one embodiment the gels can be applied topically to the skin to treat a variety of conditions such as abrasion, keratoses, inflammatory dermatoses, injury resulting from a surgical procedure, and disturbed keratinization. The gels may include therapeutic agents such as antibiotics, or antifungals for the localized and topical treatment of different skin conditions. These pentablock polymers may also be used in treatment of burns and other external injuries. The gels are useful in burn applications, since the gel layer formed on the skin provides local or transdermal delivery of drug to the burn site; maintains high moisture levels on severely burned sites, thus diminishing dehydration; adheres strongly to the damaged tissue, and is elastic, thus minimizing delamination and "peeling" of the gel dressing; and absorbs exudate from the wound. Gels may be selected which dissolve into components which are absorbable and non-toxic, which promote healing, and gel spontaneously and quickly on the burn site.

The pentablock polymers may also be applied to biological tissue, or on the surface of a medical device, to form hydrogels in a variety of surgical applications for the treatment of tissue or organs. The gel also may be applied between two surfaces, such as tissue surfaces, to adhere the surfaces. The gels may be applied to tissue such as vascular tissue, for example for the treatment of restenosis of the arteries or in angioplasty procedures. A biologically active material may be provided in the gel optionally, thereby altering the rate of drug release from the gel.

Generally speaking, the bioactive agent or diagnostic agent comprises about 0.1 to 10% by weight of the agent/polymer combination with ranges of between about 1 to 5% being preferred. As shown in the following examples, the thermosensitive gels are especially applicable to polypeptides, but is most useful for polypeptides which are relatively stable at temperatures of up to about 50° C.

Examples of suitable bioactive agents or diagnostic agents include synthetic inorganic and organic compounds, proteins and peptides, polysaccharides and other sugars, lipids, gangliosides, and nucleic acid sequences having therapeutic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoagulants, immunomodulating agents, cytotoxic agents, antibiotics, antivirals, antisense, antigens, and antibodies. Specific materials include antibiotics, antivirals, anti-inflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants and/or antithrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator ("TPA") and anisoylated plasminogen activator ("APA") and anisoylated plasminogen-streptokinase activator complex ("APSAC"), colchicine and alkylating agents, and aptomers. Specific examples of modulators of cell interactions include interleukins, platelet derived growth factor, acidic and basic fibroblast growth factor ("FGF"), transformation growth factor β ("TGF beta"), epidermal growth factor ("EGF"), insulin-like growth factor, and antibodies thereto. Specific examples of nucleic acids include genes and cDNAs encoding proteins, expression vectors, antisense and other oligonucleotides such as ribozymes which can be used to regulate or prevent gene expression. Specific examples of other bioactive agents include modified extracellular matrix components or their receptors, and lipid and cholesterol sequestrants. Typical anticancer agents include adriamycin, mitomycin, bleomycin, cisplatin, carboplatin, doxorubicin, daunorubicin, 5-fluorouracil, methotrexate, taxol, taxotere, actinomycin D, and the like. Exemplary diagnostic materials include paramagnetic molecules, fluorescent compounds, magnetic molecules, and radionuclides.

While not being specifically limited to the following, pharmaceutically useful polypeptides may be selected from group consisting of triamcinolone, acetonide, oxytocin, vasopressin, adrenocorticotrophic hormone, epidermal growth factor, platelet-derived growth factor ("PDGF"), prolactin, luliberin or luteinizing hormone releasing hormone, growth hormone, growth hormone releasing factor, insulin, somatostatin, glucagon, interleukin-2 ("IL-2"), interferon-alpha, beta, gamma, gastrin, tetragastrin, pentagastrin, urogastrone, secretin, calcitonin, enkephalins, endorphins, angiotensins, thyrotropin releasing hormone ("TRH"), tumor necrosis factor ("TNF"), nerve growth factor ("NGF"), granulocyte-colony stimulating factor ("G-CSF"), granulocyte macrophage-colony stimulating factor ("GM-CSF"), macrophage-colony stimulating factor ("M-CSF"), renin, bradykinin, bacitracins, polymixins, colistins, tyrocidine, gramicidines, monoclonal antibodies, and synthetic analogues, modifications, and pharmacologically active fragments thereof, and soluble vaccines.

In some instances, physical stability of the bioactive agent or diagnostic agent with the pentablock polymers of the present invention can also be increased by various additives to aqueous solutions of the peptide or protein drugs. Additives, such as polyols (including sugars), amino acids, proteins such as collagen and gelatin, and certain salts may be used. These additives can readily be incorporated into the reverse thermal gelation compositions of the present invention.

Pentablock Nanoparticles in Pentablock Thermosensitive Gel

In another aspect, the present invention is directed to compositions of matter in which the pentablock nanoparticles having bioactive agent or diagnostic agent incorporated therein are dispersed the pentablock thermosensitive gel. The pentablock polymer utilized for the preparation of thermosensitive gel was first dissolved in a pharmaceutically acceptable liquid, which is preferably a buffer. Preferably, the buffer comprises 10 mM phosphate buffer saline at 4° C. Typically, the concentration is about 5 to 75 wt % thermosensitive gelling pentablock polymer. Preferably, the concentration of the pentablock polymer is about 10 to 50 wt %, with about 20% wt % thermosensitive polymer solution being most preferred. After that, nanoparticles were dispersed in the thermosensitive polymer solution to form a composite formulation comprised of nanoparticles suspended in the thermosensitive gel.

Example 1

Synthesis of Pentablock Polymer for Nanoparticles

In this example, a pentablock polymer having a PGA-PCL-PEG-PCL-PGA block configuration was prepared and denominated "Pentablock Polymer A." More specifically, the pentablock polymer according to $PGA_{300}$-$PCL_{7500}$-$PEG_{1000}$-$PCL_{7500}$-$PGA_{300}$ was prepared, wherein the subscript represents theoretical molecular weight of each block.

Pentablock polymer A was prepared in two steps by sequential ring opening polymerization. In the first step, PEG of molecular weight 1,000 Da was allowed for polymerization with ε-caprolactone in presence of stannous octoate as a catalyst to form the triblock copolymer polycaprolactone-polyethylene glycol-polycaprolactone (PCL-PEG-PCL) (Scheme 1). In the second step, the triblock polymer was reacted with glycolide form the pentablock copolymer (Scheme 2).

More specifically, in the first step, PEG was dissolved in anhydrous toluene followed by distillation to remove residual moisture. Polyethylene glycol (0.001 mol) and ε-caprolactone (0.13 mol) were taken and stannous octoate (0.5 w/w % of monomer concentration) was used as catalyst. The reaction was kept at 130° C. for 24 hours and then the reaction mixture (RM) was degassed for 30 minutes. After degassing, RM was dissolved in methylene chloride followed by precipitation with petroleum ether. The precipitated polymer was filtered and dried for 24 hours in vacuum at room temperature.

Scheme 1:

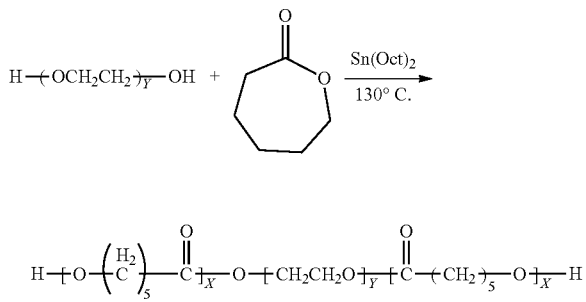

As shown in Scheme 2, for the synthesis of the pentablock polymer, the triblock copolymer was taken in a round bottom flask and glycolide (0.005 mol) was added to it and continued stirring for 24 hours at 130° C. under inert atmosphere. For sequential polymerization stannous octoate (0.5 w/w % of monomer concentration) was added as a catalyst. The final polyglycolide-polycaprolactone-polyethylene glycol-polycaprolactone-polyglycolide (PGA-PCL-PEG-PCL-PGA) compound was purified by similar precipitation method followed in the first step.

SCHEME 2:

PCL-PEG-PCL + Glycolide $\xrightarrow{\text{Sn(Oct)}_2}{130° \text{C.}}$

PGA-PCL-PEG-PCL-PGA

¹H NMR spectroscopy was performed to characterize composition of polymer. Spectra were recorded by dissolving polymeric material in CDCl₃ with Varian-400 NMR instrument. The results are shown in FIG. 1.

Example 2

Synthesis of Pentablock Polymer for Thermosensitive Gel

In this example, a pentablock polymer having a PEG-PCL-PLA-PCL-PEG block configuration was prepared and denominated "Pentablock Polymer B." More specifically, the pentablock polymer according to $PEG_{550}$-$PCL_{825}$-$PLA_{550}$-$PCL_{825}$-$PEG_{550}$ was prepared, wherein the subscript represents theoretical molecular weight of each block.

For synthesis of Pentablock Polymer B, in first step, a polyethylene glycol-polycaprolactone (PEG-PCL) diblock polymer was synthesized by ring opening polymerization of ε-caprolactone utilizing monomethoxy polyethylene glycol) (mPEG) 550 as initiator and stannous octoate as catalyst. The diblock polymer was further reacted with L-lactide from triblock polymer polylactide-polyethylene glycol-polycaprolactone (PEG-PCL-PLA). The triblock polymer was further coupled using hexamethylene diisocyanate ("HMDI") as a coupling agent, and the reaction was performed for 8 hours to synthesize final pentablock polymer PEG-PCL-PLA-PCL-PEG. The resulting final polymer was purified by dissolving in methylene chloride followed by precipitation in petroleum ether.

Briefly for the synthesis of PEG-PCL-PLA-PCL-PEG, the mPEG was dried under vacuum for 3 hours before copolymerization. Then calculated amount of mPEG (0.01 mol), ε-caprolactone (0.06 mol) and stannous octoate (0.5 w/w % of monomer concentration) were added to the reaction mixtures in a round bottom flask. The reaction was performed for 24 hours at 130° C. Then polymer was dissolved in methylene chloride and purified by fractional precipitation with petroleum ether. The purified product was vacuum dried for 48 hours to remove residual solvent. For the synthesis of triblock copolymer, the diblock copolymer was taken in a round bottom flask and L-lactide (0.01 mol) was added to it. Reaction was performed for 24 hours at 130° C. Then coupling of triblock polymer was performed by adding HDMI (0.01 mol) and reaction was continued for 6 hours at 60° C. The final polymer was dissolved in 20 ml of methylene chloride and purified by precipitation with petroleum ether. The purified product was vacuum dried for 48 hours to remove residual solvent.

Scheme 1:

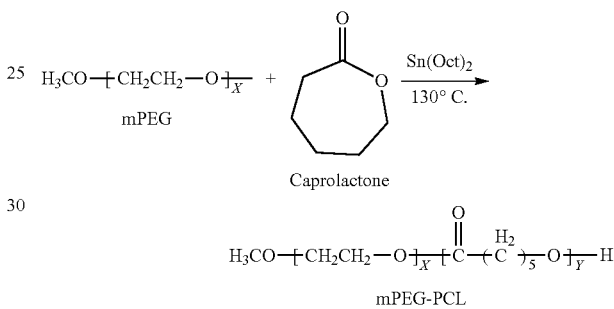

Scheme 2:

Step 1:

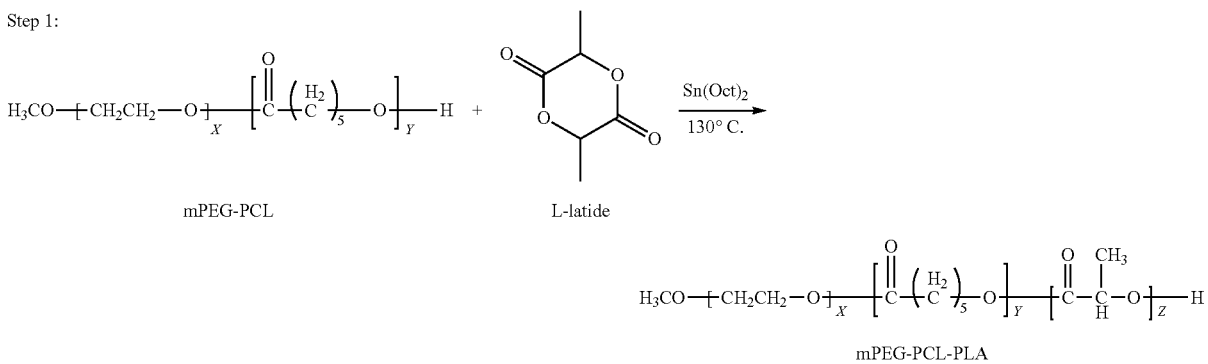

Step 2:

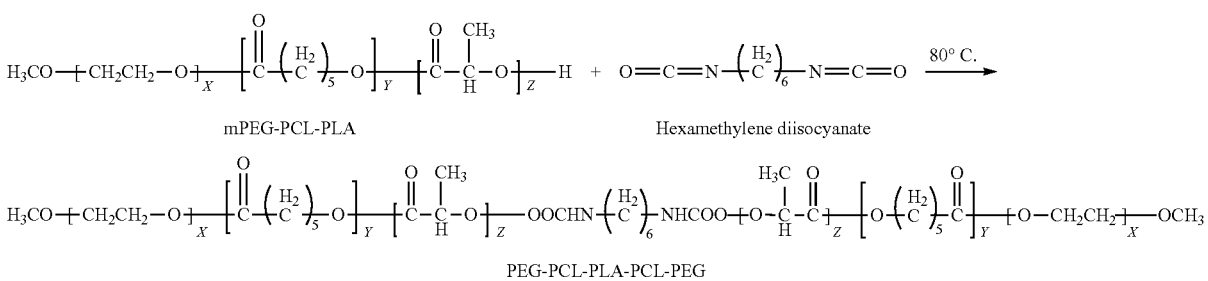

Figure 2:
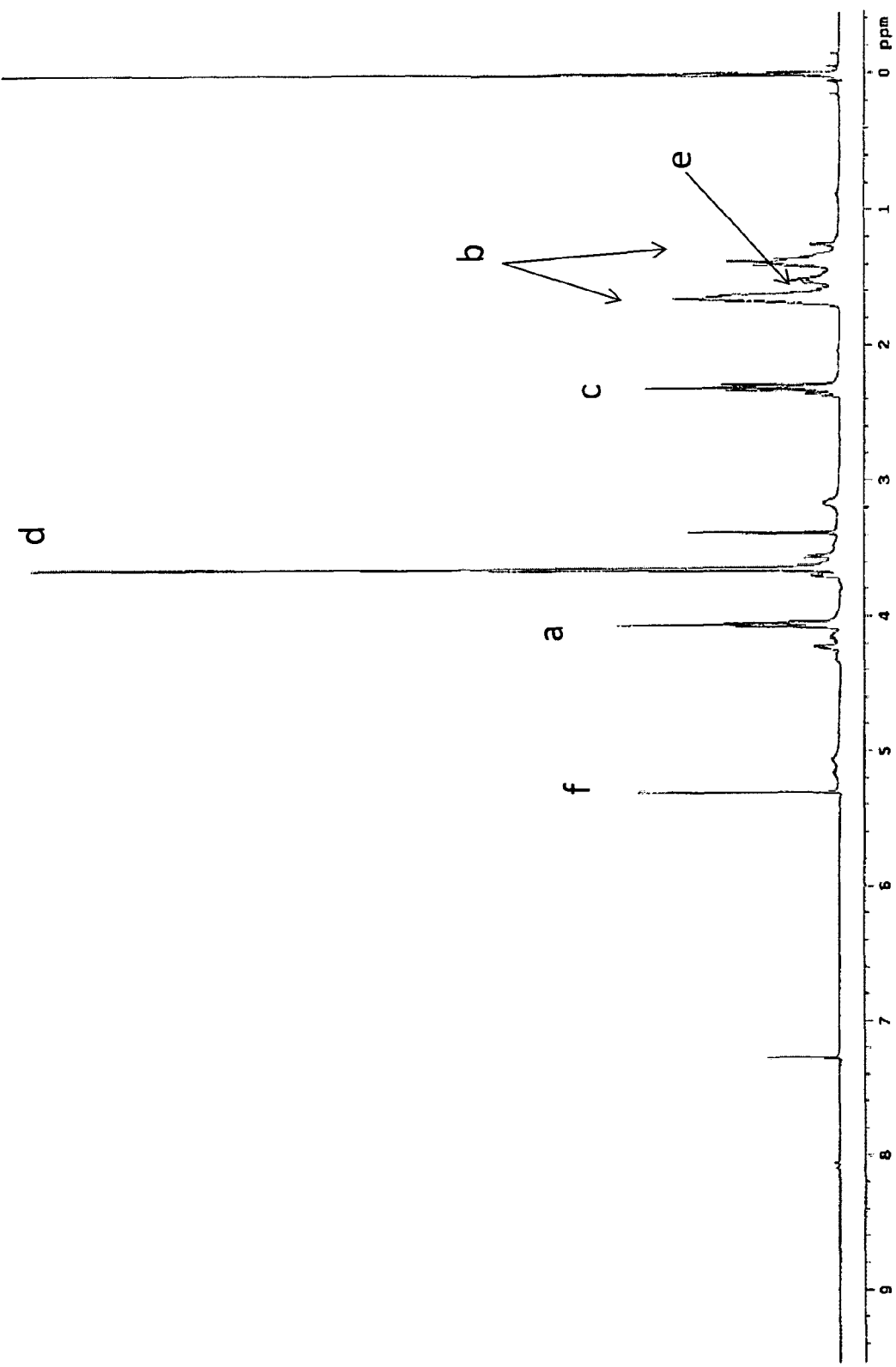
FIG. 2 shows the NMR spectra of Pentablock Polymer B ($PEG_{550}$-$PCL_{825}$-$PLA_{550}$-$PCL_{825}$-$PEG_{550}$).

¹H NMR spectroscopy was performed to characterize composition of polymer. Spectra were recorded by dissolving polymeric material in $CDCl_3$ with Varian-400 NMR instrument. The results are shown in FIG. 2.

Example 3

Cytotoxicity and Biocompatibility Studies

The cytotoxicity and biocompatibility of the Pentablock Polymer A and Pentablock Polymer B were investigated in several cell lines. ARPE-19 (human retinal pigment epithelial cell line), SIRC (rabbit corneal cell line), and RAW 264.7 (mouse macrophage cell line) were obtained from American Type Culture Collection ("ATCC"). ARPE-19 cells were cultured in Dubelcco's modified Eagle's medium ("DMEM/F12") supplemented with 10% fetal bovine serum ("FBS"), 100 U/mL penicillin and 100 µg/mL of streptomycin. SIRC cells were cultured in minimum essential medium ("MEM") and supplemented with 10% FBS, 100 U/mL of penicillin and 100 µg/mL of streptomycin. RAW 264.7 (Mouse macrophage cells) cells were cultured in DMEM/F12 supplemented with 10% FBS, 10% of nonessential amino acids, 100 U/mL penicillin and 100 µg/mL of streptomycin. The pH of the medium was adjusted to 7.4 and cells were incubated in humidified atmosphere at 37° C. temperature with 5% $CO_2$ environment. The cell cultures were exposed directly to different concentrations of Pentablock Polymer A and Pentablock Polymer B.

Pentablock Polymer A:

Two different concentrations, 2 mg/ml and 20 mg/ml, of Pentablock Polymer A were prepared in acetonitrile and 50 µL was transferred in 96 well plates. Plates were kept overnight under ultraviolet light, having one set of negative (i.e., without polymer). The plates were seeded with cell density of 10,000 cells/well. The cells were incubated for 48 hours at the humidified atmosphere for 37° C. and 5% $CO_2$.

Pentablock Polymer B:

Cytotoxicity for Pentablock Polymer B was performed at different concentration ranging from 0.5-10 mg/ml. The plates were seeded with cell density of 10,000 cells/100 µL. After 24 hours of incubation fresh medium containing hydrogel of different concentration ranging from 0.5-10 mg/ml were added and further incubated for 24 hours.

The cytotoxicity protocol for Pentablock Polymer A and B was different because Pentablock Polymer A is insoluble in water whereas Pentablock Polymer B is water soluble. To evaluate cytotoxicity, MTS assays, tumor necrosis factor alpha release studies, and IL-6 release studies were performed.

MTS Assay:

MTS assay is based on the reduction of the tetrazolium salt (yellow) to fromazone (purple) by mitochondrial enzymes of metabolic active cells. The amount of the fromazone is directly proportional to viable cells. In MTS assay Trioton X treated cells were served as negative control and untreated cells served as positive control. Then, 100 µL of serum free medium containing 20 µL of MTS solution was added to the 96 well plates, and these plates were incubated at 37° C. and 5% $CO_2$ for 4 hours. After incubation, the absorbance of each well was measured at 450 nm by ELISA plate reader. The absorbance is directly proportional to viability of cells. The results of the MTS assay are shown in the following Table 1 and Table 2.

TABLE 1

MTS assay on Pentablock Polymer A

| Cells Lines | Blank (negative control) | Polymer-A | Triton X (positive control) |
|---|---|---|---|
| RAW 264.7 (20 mg/ml) | 100 ± 0.687 | 83.773 ± 4.280 | 0 ± 0.594 |
| RAW 264.7 (2 g/ml) | | 95.269 ± 1.891 | |
| SIRC (20 mg/ml) | 100 ± 2.211 | 86.248 ± 0.968 | 0 ± 0.271 |
| SIRC (2 mg/mL) | | 98.066 ± 1.030 | |

TABLE 2

MTS assay on Pentablock Polymer B

| Cells Lines | Concentration (mg/mL) | Blank negative control | Polymer B | Triton X (positive control) |
|---|---|---|---|---|
| ARPE 19 | 0.5 | 100.000 ± 2.440 | 99.465 ± 2.889 | 0.000 ± 0.491 |
| | 1 | | 99.542 ± 5.432 | |
| | 2.5 | | 99.998 ± 4.199 | |
| | 5 | | 98.637 ± 5.595 | |
| | 10 | | 91.068 ± 1.907 | |
| PCEC | 0.5 | 100.000 ± 3.397 | 101.541 ± 7.907 | 0.000 ± 1.099 |
| | 1 | | 99.672 ± 5.077 | |
| | 2.5 | | 101.538 ± 6.378 | |
| | 5 | | 87.098 ± 4.505 | |
| | 10 | | 85.189 ± 6.677 | |

Tumor Necrosis Factor Alpha ("TNFα") Release Study:

In this example, RAW 264.7 cells were cultured and incubated as described above in cytotoxicity studies.

Pentablock Polymer A:

2 mg/ml and 20 mg/ml of the polymer solutions were prepared in acetonitrile. These polymer solutions (300 µL) were aliquot in 24 well plates, followed by overnight UV exposure. After getting 80% confluence, cells were trypsinized and 50,000 cells were seeded per well. One set of wells were kept without polymers and considered as blank. Cells were incubated for 24 hours at 37° C. and 5% $CO_2$ in humidified atmosphere. A sample volume of 120 µL was collected at 6 and 24 hours from each well and stored at −80° C. The levels of TNFα were measured by enzyme-linked immunosorbent assay ("ELISA") (eBIOSCIENCE, USA). The ELISA assay was performed as standard manufacturer protocol. Calibration curve of TNFα was prepared in the range of 10 pg/mL to 750 pg/mL and absorbance was measured at 450 nm by ELISA plate reader. The results are shown in Table 3:

TABLE 3

TNFα release study of Pentablock Polymer A

| Cells Lines | Blank | Polymer-A | LPS (Positive control) |
|---|---|---|---|
| RAW 264.7 (20 mg/ml) | 220.841 ± 38.863 | 233.628 ± 42.461 | 716.601 ± 34.994 |
| RAW 264.7 (2 mg/ml) | | 183.833 ± 11.911 | |

Pentablock Polymer B:

TNFα release study of Pentablock Polymer B was performed at different concentration ranging from 0.5-10 mg/ml. The plates were seeded with cell density of 50,000 cells per well. After 24 hours of incubation fresh medium containing hydrogel of different concentration ranging from 0.5-10 mg/ml were added and further incubated for 24 hours. After 24 hours of exposure, 120 μL was collected from each well and stored at −80° C. The levels of TNFα were measured by enzyme-linked immunosorbent assay ("ELISA") (eBIOSCIENCE, USA). The ELISA assay was performed as standard manufacturer protocol. Calibration curve of TNFα was prepared in the range of 10 pg/mL to 750 pg/mL and absorbance was measured at 450 nm by ELISA plate reader. The results are shown in Table 4:

TABLE 4

TNFα release study of Pentablock Polymer B

| Cells Lines | Concentration (mg/mL) | Blank (negative control) | Polymer B | LPS (positive control) |
|---|---|---|---|---|
| RAW 264.7 | 0.5 | 344.664 ± 19.419 | 374.279 ± 47.088 | 1963.750 ± 00.000 |
| | 1 | | 353.993 ± 53.655 | |
| | 2.5 | | 390.464 ± 35.735 | |
| | 5 | | 406.636 ± 47.602 | |
| | 10 | | 415.857 ± 52.765 | |

IL-6 Release Study:

Pentablock Polymer A:

In this example, RAW 264.7 cells were cultured and incubated as described above in cytotoxicity studies.

RAW 264.7 cells were cultured and incubated just as explained in cytotoxicity study. 2 mg/ml and 20 mg/ml of the polymer solutions were prepared in acetonitrile. 300 μl of these solutions were aliquot in 24 well plates and kept overnight under UV exposure for sterilization. Cells were trypsinized at 80% of confluence and 50,000 cells were plated per well. Cells were incubated for 24 hours at 37° C. and 5% CO$_2$ in humidified atmosphere. After 24 hours of exposure 100 μL of supernatant were taken from each well and analyzed for the levels of Interleukin 6 by ELISA (eBIOSCIENCE, Inc.) assay kit. The assays were performed according to standard sandwich ELISA protocol given by manufacturer. Calibration curves for Interleukin 6 and Interleukin 1β were performed in the range of 5 pg/mL to 500 pg/mL. Absorbances were measured at 450 nm by 96 well plate reader.

TABLE 5

IL-6 release study of Pentablock Polmer A

| Cells Lines | Blank (negative control) | PB-A | LPS (Positive control) |
|---|---|---|---|
| RAW 264.7 (20 mg/mL) | 7.714 ± 0.984 | 7.116 ± 1.848 | 327.090 ± 27.414 |
| RAW 264.7 (2 mg/mL) | | 6.630 ± 0.879 | |

Pentablock Polymer B:

IL-6 release study of Pentablock Polymer B was performed at different concentration ranging from 0.5-10 mg/ml. The plates were seeded with cell density of 50,000 cells per well. After 24 hours of incubation fresh medium containing hydrogel of different concentration ranging from 0.5-10 mg/ml were added and further incubated for 24 hours. After 24 hours of exposure, 100 μl of supernatant were taken from each well and analyzed for the levels of Interleukin 6 by ELISA (eBIOSCIENCE, Inc.) assay kit. The assays were performed according to standard sandwich ELISA protocol given by manufacturer. Calibration curves for Interleukin 6 were performed in the range of 5 pg/mL to 500 pg/mL. Absorbances were measured at 450 nm by 96 well plate reader.

TABLE 6

IL-6 release study of Pentablock Polymer B

| Cell Lines | Concentration (mg/mL) | Blank (negative control) | Polymer B | LPS (positive control) |
|---|---|---|---|---|
| RAW 264.7 | 0.5 | 344.664 ± 19.419 | 374.279 ± 47.088 | 1963.750 ± 00.000 |
| | 1 | | 353.993 ± 53.655 | |
| | 2.5 | | 390.464 ± 35.735 | |
| | 5 | | 406.636 ± 47.602 | |

Example 4

Drug Encapsulation in Pentablock Polymeric Nanoparticles

In this example, two different exemplary drugs were encapsulated into nanoparticles of Pentablock Polymer A.

Preparation of Prednisolone Nanoparticles of Pentablock Polymer A:

Nanoparticles were prepared by single emulsification method using the Pentablock Polymer A. Briefly, 100 mg of Pentablock Polymer A and the 10 mg prednisolone were dissolved in methylene chloride. The resulting oil phase was emulsified in 2.0 w/v % aqueous solution of polyvinyl alcohol with the help of a tip sonicator at 60 W for 5 minutes to form oil in water (o/w) emulsion. The resulting organic solvent was evaporated under vacuum to form nanoparticles. The unreacted drug and PVA residue were washed three times with deionized water and the nanoparticles were collected by ultracentrifugation at 21,000 RPM for one hour. The drug entrapment efficiency was determined using high performance liquid chromatography (HPLC) using C-18 reverse-phase column at 254 nm, and was 40±5%. The particle size was characterized by dynamic light scattering, and was 220±5 nm.

Preparation of FITC-IgG Nanoparticles of Pentablock Polymer A:

Nanoparticles were prepared by double emulsification method. First an aqueous solution 10 mg of FITC-IgG was first emulsified in methylene chloride containing the pentablock polymer. The resulting o/w emulsion was then poured in 2.0 w/v % aqueous PVA solution resulting in the formation of second water-in-oil-in-water (w/o/w) emulsion. After evaporation of methylene chloride the nanoparticles were isolated by centrifugation at 21,000 RPM for one hour. After washing for three times with deionized water nanoparticles were lyophilized for further use. The drug entrapment efficiency was determined using fluorescence spectroscopy at absorption wavelength of 492 nm and emission wavelength of 518 nm.

Example 5

Sol-Gel Transition Studies of Polymer-B

Figure 3:
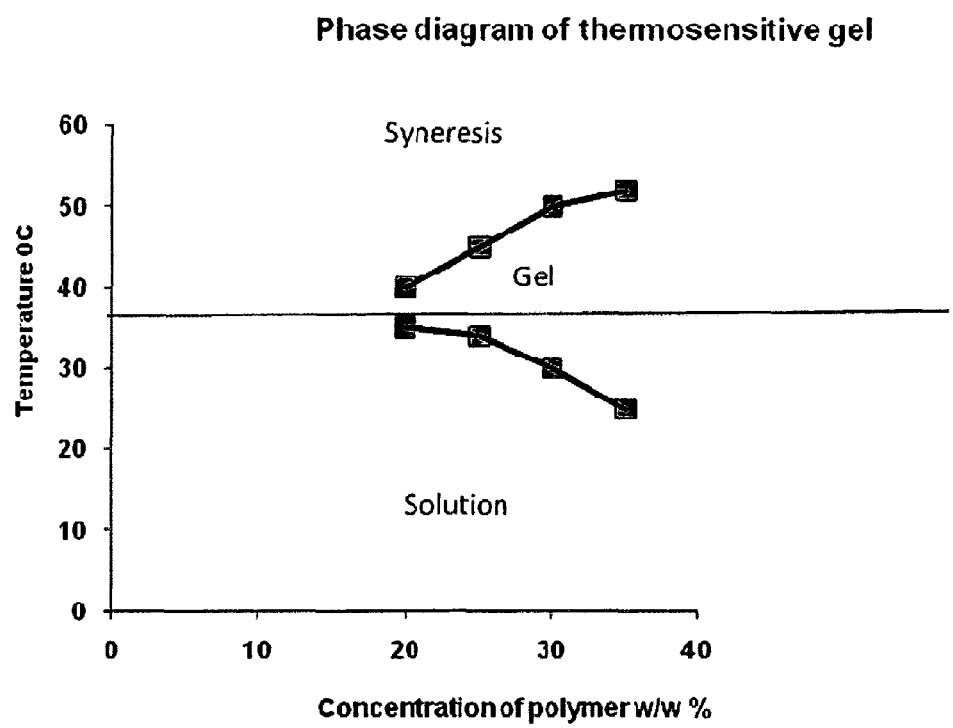
FIG. 3 shows a phase diagram showing the sol-gel transition studies of the Pentablock Polymer B.

In this example, a sol-gel transition study was performed by test tube inverting method. First, the Pentablock Polymer B was solubilized in PBS by keeping overnight at 4° C. Then 0.5 ml of polymer solution was kept in 4 ml tube at designated temperature for 20 minutes. The gel formation was characterized visually by inverting the tube. The physical state of flow is characterized as sol phase whereas the state of no flow is characterized as gel phase. Polymer solutions of different concentrations were heated from 24° C. to 40° C. and gel formation was analyzed. The results are shown in FIG. 3.

Example 6

In Vitro Release Studies from Pentablock Polymer A Nanoparticles

Figure 4:
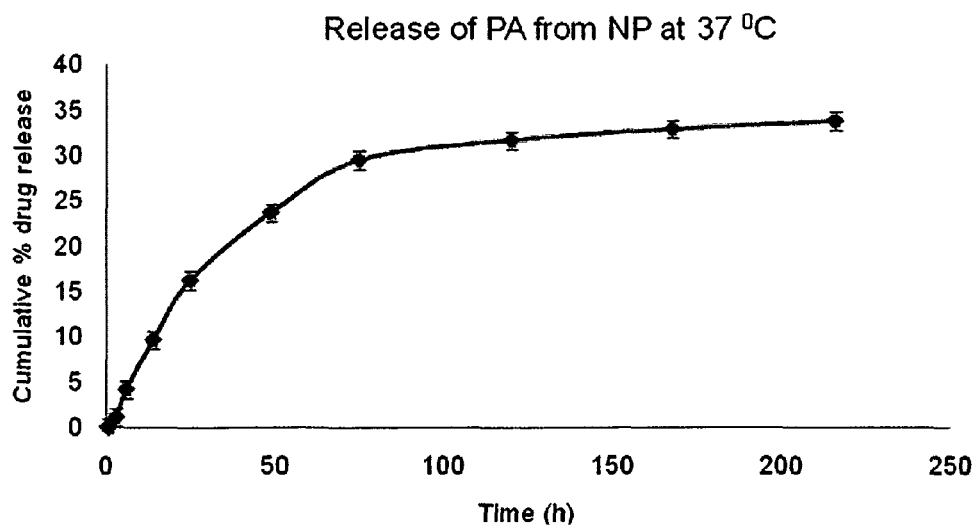
FIG. 4 shows the in vitro release profile of prednisolone acetate ("PA") from Pentablock Polymer A nanoparticles at 37° C. (n=3).

In this example, 20 mg of prednisolone nanoparticles prepared from Pentablock Polymer A as described in Example 4 were dispersed in 500 µl of 0.1 M phosphate buffer saline (pH 7.4). The prepared solution was then added into the dialysis bag (MW cutoff 12,500) which was kept in a 15 ml tube containing 10 ml of release medium at 37° C. The entire release medium was replaced with fresh buffer at designated intervals to mimic the sink condition. The samples were stored at −20° C. before further analysis. The release samples were analyzed by HPLC. The results are shown in FIG. 4.

Figure 5:
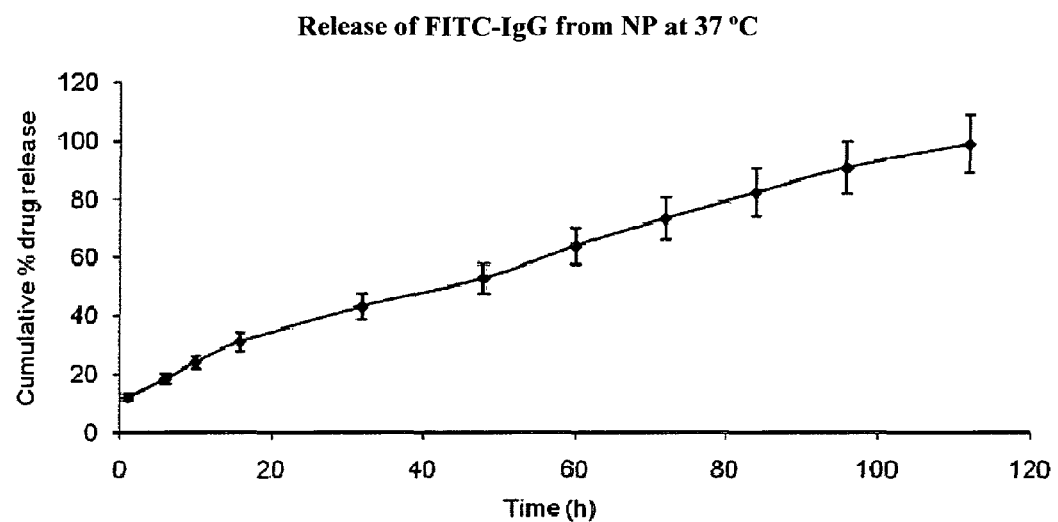
FIG. 5 shows the in vitro release profile of FITC-IgG from pentablock A nanoparticles at 37° C. (n=3).

Next, 20 mg of FITC-IgG nanoparticles prepared from Pentablock Polymer A as prepared in Example 4 were dispersed in 10 ml of 0.1 M phosphate buffer saline (pH 7.4). The prepared solution was kept at 37° C. in a 30 ml centrifuge tube. At designated time intervals tube was taken out from water bath and centrifuged at 10,000 rpm and entire release medium was replaced with fresh buffer. The samples were stored at −20° C. before further analysis. The release samples were analyzed by fluorescence spectroscopy at absorption wavelength of 492 nm and emission wavelength of 518 nm. The results are shown in FIG. 5.

Example 7

Drug Release from Pentablock Polymer B Gel

Figure 6:
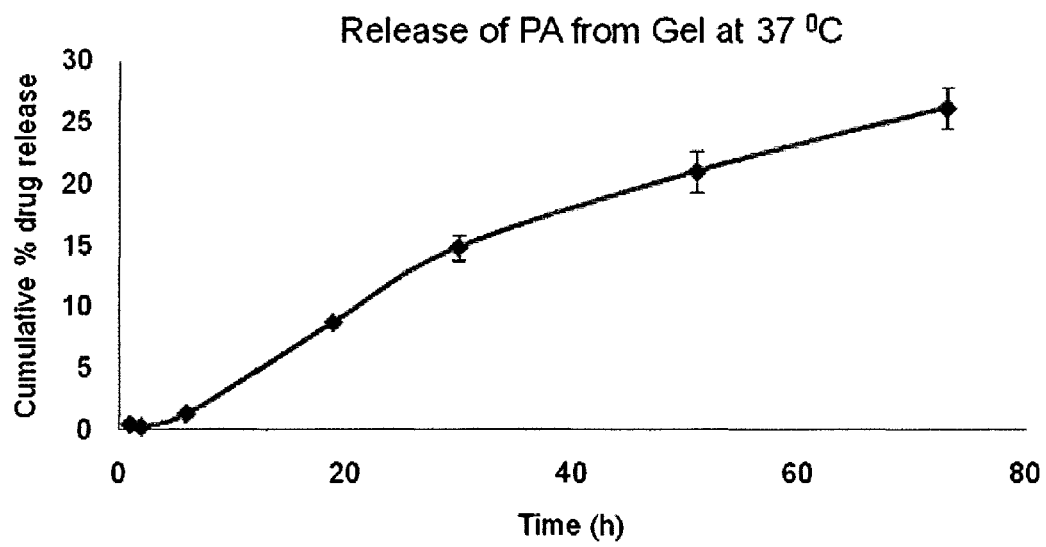
FIG. 6 shows the in vitro release profile of PA suspended in thermosensitive gel at 37° C. (n=3).

In this example, a 20% w/w Pentablock Polymer B and 250 µg prednisolone acetate was solubilized in 10 mM PBS by keeping overnight at 4° C. At this temperature, the composition is in a liquid phase. The prepared solution was then added into the dialysis bag (MW cutoff 12,500) which was kept in a 10 ml tube containing 5 ml of release medium at 37° C. Upon raising the temperature, the polymer solution forms a gel having the drug incorporated into the polymer gel matrix, which is slowly released in to the release medium. The entire release medium was replaced with fresh buffer at designated intervals to mimic the sink condition. The samples were stored at −20° C. before further analysis. The release samples were analyzed by HPLC. The results are shown in FIG. 6. The release kinetics are close to zero order, with about 25% of the drug being released after about 70 minutes.

Example 8

Figure 7:
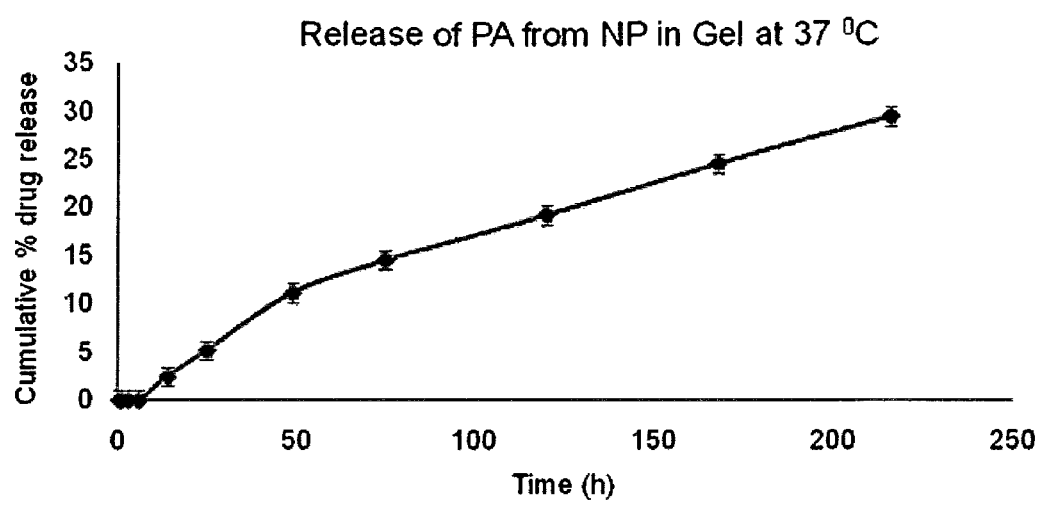
FIG. 7 shows the in vitro release profile of PA nanoparticles suspended in thermosensitive gel at 37° C. (n=3).

Drug Release from Pentablock Polymer A Nanoparticles Dispersed in Pentablock Polymer B Gel In this example, 20% w/w of Pentablock Polymer B was solubilized in 10 mM PBS by keeping overnight at 4° C. Then prednisolone acetate nanoparticles (140 mg) drug equivalent to 250 µg, prepared from Pentablock Polymer A were dispersed in 20% w/w thermosensitive polymer solution. Thus, the entire composition takes the form of an injectable formulation. The prepared solution was then added into the dialysis bag (MW cutoff 12,500) which was kept in a 10 ml tube containing 5 ml of release medium at 37° C. The entire release medium was replaced with fresh buffer at designated intervals to mimic the sink condition. The samples were stored at −20° C. before further analysis. The release samples were analyzed by HPLC. The results are shown in FIG. 7. The release kinetics are first order, but the release time is over twice as long as when the gel is used alone (Example 7).

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A pentablock polymer according to the formula $$PGAz-PCLy-PEGx-PCLy-PGAz,$$

wherein PEG is polyethylene glycol;
wherein PCL is poly(ε-caprolactone);
wherein PGA is polyglycolic acid;
wherein X defines an average molecular weight of 200 to 20,000 Da;
wherein Y defines an average molecular weight of 1,000 to 20,000 Da; and
wherein Z defines an average molecular weight of 100 to 5,000 Da.

2. The pentablock polymer of claim 1,
wherein X defines an average molecular weight of 500 to 5,000 Da; or wherein Y defines an average molecular weight of 2,500 to 15,000 Da; or
wherein Z defines an average molecular weight of 200 to 1,000 Da.

3. The pentablock polymer of claim 1,
wherein X defines an average molecular weight of 500 to 1,500 Da; or
wherein Y defines an average molecular weight of 5,000 to 10,000 Da; or
wherein Z defines an average molecular weight of 200 to 500 Da.

4. A nanoparticle comprising the pentablock polymer of claim 1.

5. A bioactive agent or diagnostic agent composition consisting essentially of the pentablock polymer of claim 1 and an effective amount of a bioactive agent or diagnostic agent.

6. The bioactive or diagnostic agent composition of claim 5 wherein said bioactive agent or diagnostic agent comprises a protein or peptide.

7. The nanoparticle of claim 4 wherein said nanoparticle has a particle size less than 1 micron.

8. The nanoparticle of claim 4 wherein the nanoparticle has a particle size of 300 to 700 nm.

9. The nanoparticle of claim 4 wherein the nanoparticle has a particle size of 400 to 600 nm.

10. The nanoparticle of claim 4 wherein the PEG is less than 10% by weight, the PCL is greater than 80% by weight, and the PGA is less than 10% by weight.

11. The composition of claim 5 wherein said bioactive agent or diagnostic agent comprises about 1 to 5 wt %.

12. The composition of claim 5 wherein said bioactive agent is prednisolone.

13. A pentablock polymer according to the formula

PEG-PCL-PLA-PCL-PEG, wherein PEG is polyethylene glycol having an average molecular weight of 100 to 20,000 Da;
wherein PCL is poly(ε-caprolactone) having an average molecular weight of 100 to 1,000 Da; and
wherein PLA is polyglycolic acid having an average molecular weight of 100 to 5,000 Da.

14. The pentablock polymer of claim 13,
wherein PEG has an average molecular weight of 200 to 5,000 Da; or
wherein PCL has an average molecular weight of 200 to 900 Da; or
wherein PLA defines an average molecular weight of 200 to 1000 Da.

15. The pentablock polymer of claim 13,
wherein PEG has an average molecular weight of 300 to 2,000 Da; or
wherein PCL has an average molecular weight of 600 to 850 Da; or
wherein PLA defines an average molecular weight of 200 to 800 Da.

16. A thermosensitive gel comprising the pentablock polymer of claim 13.

17. A bioactive agent or diagnostic agent composition consisting essentially of the pentablock polymer of claim 13 and an effective amount of a bioactive agent or diagnostic agent.

18. A pentablock polymer according to the formula CBABC, comprising:
polyethylene glycol (PEG);
poly(ε-caprolactone) (PCL); and
polyglycolic acid (PGA) or polylactic acid (PLA);
wherein the pentablock polymer is in the form of nanoparticles when having a PGA-PCL-PEG-PCL-PGA configuration; and
wherein the pentablock polymer is in the form of thermosensitive gel when having a PEG-PCL-PLA-PCL-PEG configuration.

19. The pentablock polymer of claim 18, wherein when the pentablock polymer has the PGA-PCL-PEG-PCL-PGA configuration,
the PEG has an average molecular weight of 200 to 20,000 Da;
the PCL an average molecular weight of 1,000 to 20,000 Da; and
the PGA has an average molecular weight of 100 to 5,000 Da.

20. The pentablock polymer of claim 18, wherein when the pentablock polymer has the PEG-PCL-PLA-PCL-PEG configuration,
the PEG has an average molecular weight of 100 to 20,000 Da;
the PCL an average molecular weight of 100 to 1,000 Da; and
the PLA has an average molecular weight of 100 to 5,000 Da.

* * * * *